United States Patent
Grueebler et al.

(10) Patent No.: US 11,395,713 B2
(45) Date of Patent: Jul. 26, 2022

(54) ILLUMINATED CANNULA

(71) Applicant: Alcon Inc., Fribourg (CH)

(72) Inventors: Reto Grueebler, Greifensee (CH); Niels Alexander Abt, Winterhur (CH)

(73) Assignee: Alcon Inc., Fribourg (CH)

( * ) Notice: Subject to any disclaimer, the term of this patent is extended or adjusted under 35 U.S.C. 154(b) by 452 days.

(21) Appl. No.: 16/512,877

(22) Filed: Jul. 16, 2019

(65) Prior Publication Data

US 2020/0022773 A1    Jan. 23, 2020

Related U.S. Application Data

(60) Provisional application No. 62/700,607, filed on Jul. 19, 2018.

(51) Int. Cl.
  *A61B 17/34*    (2006.01)
  *A61F 9/007*    (2006.01)
  *A61B 90/30*    (2016.01)
  *A61B 3/00*     (2006.01)

(52) U.S. Cl.
  CPC ............ *A61B 90/30* (2016.02); *A61B 3/0008* (2013.01); *A61F 9/007* (2013.01); *A61B 17/3423* (2013.01); *A61B 2090/306* (2016.02)

(58) Field of Classification Search
  CPC .................. A61B 90/30; A61B 3/0008; A61B 2090/306; A61B 17/3423; A61F 9/007
  See application file for complete search history.

(56) References Cited

U.S. PATENT DOCUMENTS

| | | | |
|---|---|---|---|
| 5,201,730 A | 4/1993 | Easley | |
| 5,275,593 A | 1/1994 | Easley et al. | |
| 5,425,730 A * | 6/1995 | Luloh | A61F 9/00736 606/4 |
| 5,591,160 A | 1/1997 | Reynard | |
| 5,651,783 A | 7/1997 | Raynard | |
| 6,387,044 B1 * | 5/2002 | Tachibana | A61B 1/00135 600/114 |
| 7,223,233 B2 * | 5/2007 | Branch | A61B 17/0218 600/245 |
| 7,783,346 B2 | 8/2010 | Smith et al. | |
| 7,901,353 B2 * | 3/2011 | Vayser | A61B 1/3132 606/17 |
| 8,702,602 B2 * | 4/2014 | Berci | A61B 90/30 600/101 |
| 8,795,162 B2 * | 8/2014 | Vayser | A61B 1/00135 600/184 |
| 8,900,139 B2 | 12/2014 | Yadlowsky | |

(Continued)

OTHER PUBLICATIONS

Alcon Global Vitreoretinal Product Catalog, Feb. 2014 (59 pages).

*Primary Examiner* — Kevin T Truong
*Assistant Examiner* — Tracy L Kamikawa

(57) ABSTRACT

Apparatuses, systems, and methods for illuminating an interior portion of an eye are disclosed herein. In an exemplary aspect, the present disclosure is directed to an apparatus for use in ophthalmic surgery. The apparatus may include a light guide including an optical fiber, a transition region, and a light sleeve. The transition region may be disposed between the optical fiber and the light sleeve for transmission of light from the optical fiber to the light sleeve such that the light sleeve is operable to emit the light at a distal end of the light sleeve.

10 Claims, 6 Drawing Sheets

(56) References Cited

U.S. PATENT DOCUMENTS

| | | |
|---|---|---|
| 8,968,347 B2 | 3/2015 | McCollam |
| 9,055,885 B2 | 6/2015 | Horvath |
| 9,066,678 B2 | 6/2015 | Auld |
| 9,089,364 B2 | 7/2015 | Bhadri |
| 9,364,982 B2 * | 6/2016 | Schaller .............. A61F 9/00736 |
| 9,402,643 B2 | 8/2016 | Auld |
| 9,561,085 B2 | 2/2017 | Yadlowsky |
| 9,839,749 B2 | 12/2017 | Johnson |
| 9,956,053 B2 | 5/2018 | Diao |
| 10,016,248 B2 | 7/2018 | Mirsepassi |
| 10,039,669 B2 | 8/2018 | Heeren |
| 10,244,931 B2 | 4/2019 | Kern |
| 10,307,290 B2 | 6/2019 | Kern |
| 10,376,414 B2 | 8/2019 | Hallen |
| 10,610,408 B2 | 4/2020 | Farley |
| 2007/0100210 A1 * | 5/2007 | Selover .................. A61B 17/02 600/199 |
| 2009/0161384 A1 | 6/2009 | Smith |
| 2014/0121469 A1 * | 5/2014 | Meckel ............... A61F 9/00821 600/249 |
| 2016/0302878 A1 | 10/2016 | Kern |
| 2017/0014023 A1 | 1/2017 | Kern |
| 2017/0014267 A1 | 1/2017 | Kern |
| 2017/0119491 A1 | 5/2017 | Mirsepassi |
| 2017/0165114 A1 | 6/2017 | Hallen |
| 2018/0055596 A1 | 3/2018 | Johnson |
| 2018/0132963 A1 | 5/2018 | Diao |
| 2018/0133057 A1 | 5/2018 | Diao |
| 2018/0168768 A1 | 6/2018 | Mirsepassi |
| 2018/0168861 A1 | 6/2018 | Mirsepassi |
| 2018/0338776 A1 | 11/2018 | Farley |
| 2018/0338859 A1 | 11/2018 | Mirsepassi |
| 2018/0338860 A1 | 11/2018 | Farley |
| 2019/0239979 A1 | 8/2019 | Abt |
| 2019/0307527 A1 | 10/2019 | Grueebler |

* cited by examiner

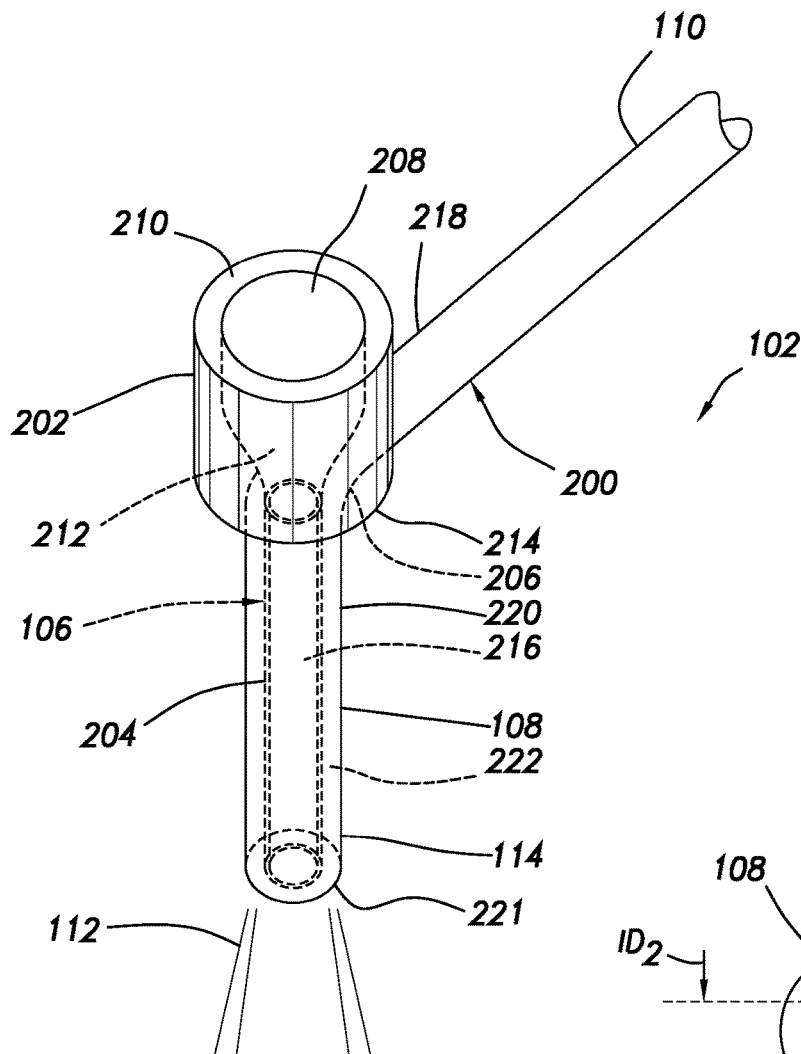
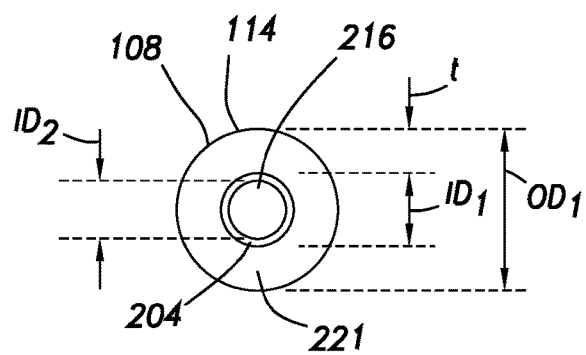
FIG.3A
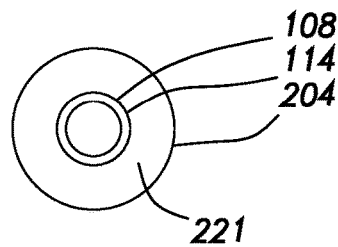
FIG.3B

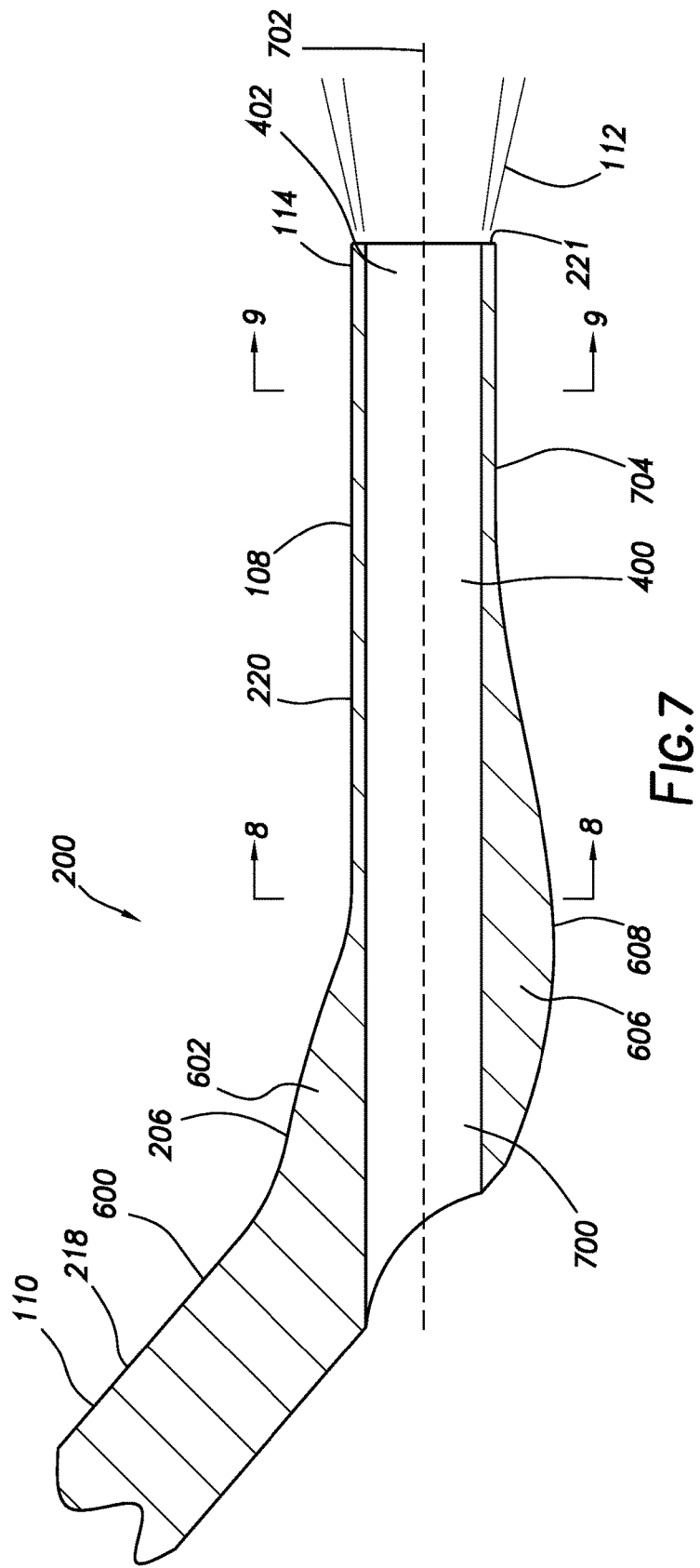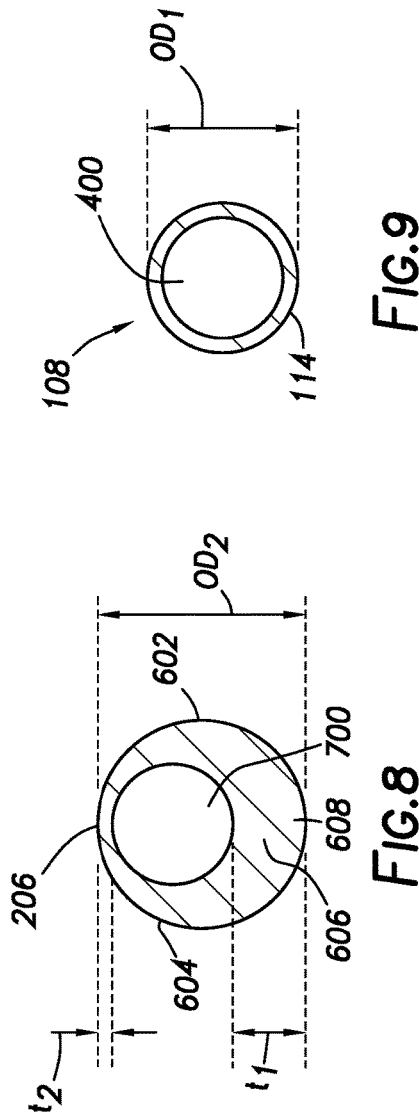
FIG. 7
FIG. 8
FIG. 9

ILLUMINATED CANNULA

CROSS-REFERENCE TO RELATED APPLICATIONS

This application claims the benefit of U.S. Provisional Application No. 62/700,607, filed Jul. 19, 2018, the entire contents of which are incorporated herein by reference.

BACKGROUND

The human eye can suffer a number of maladies causing mild deterioration to complete loss of vision. While contact lenses and eyeglasses can compensate for some ailments, ophthalmic surgery is required for others. Generally, ophthalmic surgery is classified into posterior segment procedures, such as vitreoretinal surgery, and anterior segment procedures, such as cataract surgery. Vitreoretinal surgery may address many different eye conditions, including, but not limited to, macular degeneration, diabetic retinopathy, diabetic vitreous hemorrhage, macular hole, detached retina, epiretinal membrane, and cytomegalovirus retinitis.

During ophthalmic posterior segment surgery, the surgeon may successively use different hand pieces or instruments. A surgical procedure may require that these instruments be inserted into and removed from an incision. Repeated removal and insertion of instruments may cause trauma to the eye at the incision site. To reduce such trauma and allow repeated access to the incision site, hubbed cannulas have been developed and used to help protect the incision site. These devices may include a narrow tube with an attached hub. The tube may be inserted into an incision in the eye up to the hub, which may act as a stop to prevent the tube from entering the eye completely. The hub may be stitched to the eye to prevent inadvertent removal. In addition to the hubbed cannulas, infusion cannulas may also be used through which fluids may be introduced into the eye.

To visualize the posterior segment of the eye, illumination may be needed in the interior of the eye. For example, the surgeon may need to insert and position a light source to illuminate an interior region of the eye, while simultaneously inserting and positioning a surgical hand piece for cutting and aspirating tissue from the illuminated region. Suitable light sources may include a light probe or a chandelier light. Typically, the light probe or chandelier light may require an additional incision, causing trauma to the eye at the incision site.

SUMMARY

A first aspect of the present disclosure is directed to an illuminated cannula assembly for use in ophthalmic surgery. The illuminated cannula assembly may include a light guide. The light guide may include an optical fiber, a light sleeve, and a transition region the transition region joining the optical fiber and the light sleeve and adapted to transmit light from the optical fiber to the light sleeve. The light sleeve is adapted to emit the light from a distal end thereof.

Another aspect is directed to an ophthalmic surgical illumination system that may include a light source operable to generate light; an illuminated cannula assembly operable to receive the light generated by the light source, and a cannula. The illuminated cannula assembly may include a light guide. The light guide may include an optical fiber coupled to the light source, a light sleeve, and a transition region joining the optical fiber and the light sleeve. The transition region may be configured to transmit the light from the optical fiber to the light sleeve. The light sleeve may be operable to emit the light from a distal end thereof. The cannula may include a tubing and a proximal hub disposed at a proximal end of the tubing. The light sleeve may be disposed around the tubing.

Another aspect of the disclosure is directed to a method for illuminating an interior of an eye. The method may include disposing an illuminated cannula assembly into the eye. The illuminated cannula assembly may include a light guide. The light guide may include an optical fiber, a light sleeve, and a transition region that joins the optical fiber and the light sleeve. The light sleeve may extend into an interior portion of the eye. The method may also include transmitting light through the optical fiber to the transition region and into the light sleeve such that the light emits from a distal end of the light sleeve into the interior of the eye.

The different aspects may include one or more of the following features. A cannula may include a tubing, and the light sleeve may be disposed around the tubing. The cannula may include a proximal hub disposed at a proximal end of the tubing. The transition region may branch to form a first branch and a second branch that wrap around the tubing. The first branch and the second branch may join along a first side of the tubing opposite the optical fiber at an enlarged portion of the transition region. The enlarged portion may include a bulge. The light sleeve may be disposed inside the tubing.

The different aspects may also include one or more of the following features. The enlarged portion may include a bulge formed on the first side of the transition inner lumen. An outer diameter of the transition region at the bulge may be at least 20% larger than an outer diameter of the light sleeve at a distal end of the light sleeve. The light sleeve may define an inner lumen, and the inner lumen may be in fluid communication with the transition inner lumen. An opening may be formed at a proximal end of the proximal hub. A through bore may extend from the opening to a distal end of the proximal hub. The through bore may be tapered. The transition region of the light guide may be adjacent to the proximal hub. The transition region may branch to form a first branch and a second branch that joins to encircle around the tubing. An outer diameter of the transition region at the bulge may be at least 20% larger than an outer diameter of the light sleeve at a distal end of the light sleeve. A fluid may be introduced into the interior of the eye through an inner lumen of the light sleeve. An inner surface of the light sleeve may define inner lumen that contacts the fluid introduced into the interior of the eye. A cannula may include a tubing and a proximal hub disposed at a proximal end of the tubing. The light sleeve may be disposed around the tubing. The transition region may branch to form a first branch and a second branch that wrap around the tubing and join together on a first side of the tubing opposite a second side where the optical fiber connects to the transition region. The enlarged portion may include a bulge.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The drawings illustrate certain aspects of some embodiments of the present disclosure. However, the drawings are

FIG. 2 illustrates an example illuminated cannula assembly.

FIG. 3A illustrates an end view of the cannula assembly of FIG. 2.

FIG. 3B illustrates an end view of another embodiment of a cannula assembly.

FIG. 7 is a longitudinal cross-sectional view of the light guide of FIG. 6 taken along line 7-7.

FIG. 8 is a transverse cross-sectional view taken along line 8-8 of FIG. 7.

FIG. 9 is a transverse cross-sectional view taken along line 9-9 of FIG. 7.

DETAILED DESCRIPTION

Figure 1:
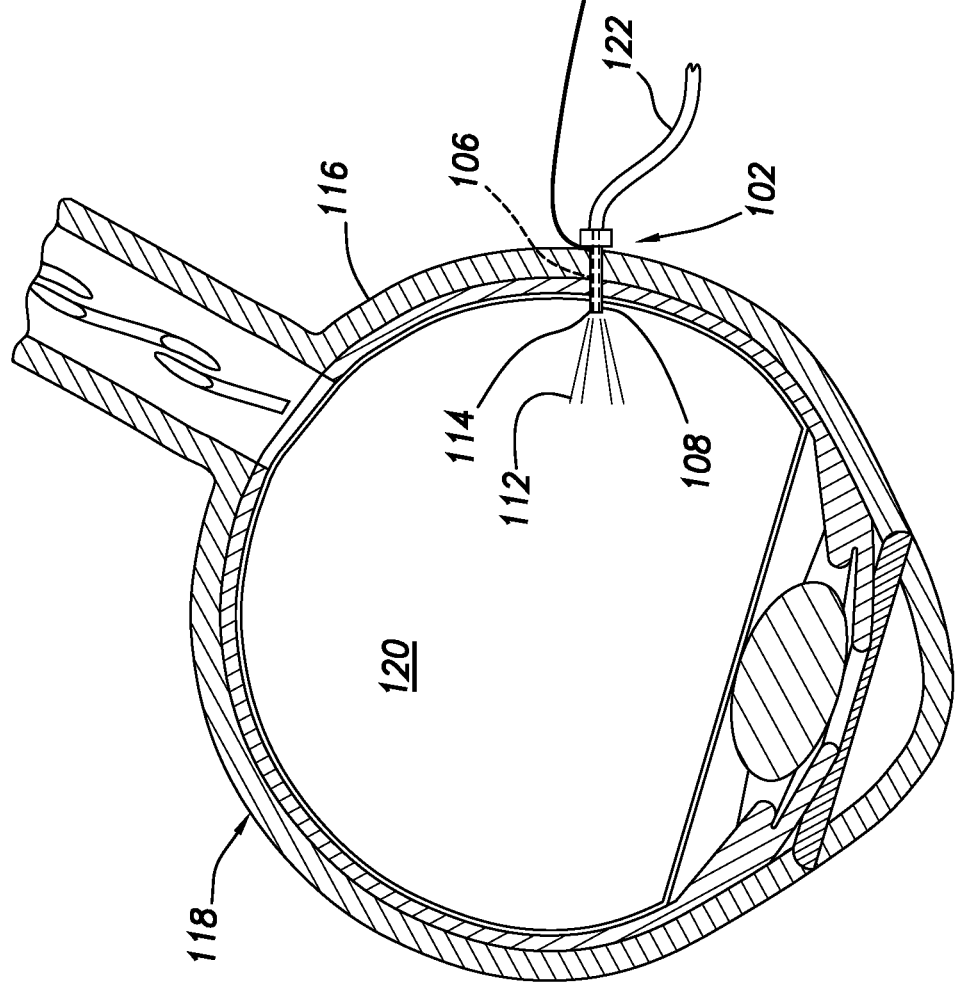
FIG. 1 illustrates an example surgical system that includes an illuminated cannula assembly.

In the following description, details are set forth by way of example to facilitate an understanding of the disclosed subject matter. It should be apparent to a person of ordinary skill in the art, however, that the disclosed embodiments are exemplary and not exhaustive of all possible embodiments.

For the purposes of promoting an understanding of the principles of the present disclosure, reference will now be made to the embodiments illustrated in the drawings and specific language will be used to describe them. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with reference to one or more embodiments may be combined with the features, components, and/or steps described with reference to other embodiments of the present disclosure. For simplicity, in some instances the same reference numbers are used throughout the drawings to refer to the same or like parts.

Embodiments described herein generally relate to eye surgery. More particularly, embodiments generally relate to illumination of the interior of an eye with a cannula. However, the scope of the disclosure is not so limited. Rather, the illumination concepts describes herein may be applicable to other areas of the medical arts or areas outside of the medical arts, and the present disclosure is intended to encompass all applicable fields.

Embodiments include illuminated cannula assemblies that includes a cannula assembly and a light sleeve. In some embodiments, the light sleeve may be disposed around the cannula or integrated into the cannula itself. For example, the light sleeve may form the lumen through which fluids or instruments may be introduced free from any intervening tubing. Light may be emitted from a distal end of the light sleeve to illuminate the interior of the eye. In some embodiments, light may be emitted along an entire circumference of the light sleeve, which may, in some instances, provide uniform light distribution. In other instances, the light emitted by the entire circumference of the light sleeve may provide a non-uniform light distribution. An illuminated cannula assembly may be of any type for use in eye surgery, including, but not limited to, an infusion cannula for introduction of fluids or a hubbed cannula for use with a trocar blade. By incorporation of the light sleeve into the cannula assembly, the requirement for an extra incision for insertion of a light source may be eliminated.

FIG. 1 illustrates an embodiment of a system 100 that includes an illuminated cannula assembly 102 and a light source 104. As illustrated, the illuminated cannula assembly 102 includes a cannula 106 and a light sleeve 108. In the illustrated embodiment, the light sleeve 108 is disposed around the cannula 106. An optical fiber 110 optically couples the light source 104 to the light sleeve 108. Light 112 from the light source 104 travels through the optical fiber 110 to the light sleeve 108. The light 112 is emitted from a distal end 114 of the light sleeve 108. As illustrated, the cannula 106 with the light sleeve 108 be inserted through sclera 116 of eye 118. In the illustrated embodiment, the cannula 106 with the light sleeve 108 is inserted through the sclera 116 such that the distal end 114 of the light sleeve 108 is disposed in an interior portion 120 of the eye 118. The light 112 is emanated from the distal end 114 of the light sleeve 108 to illuminate the interior portion 120 of the eye 118. An infusion line 122 is coupled to illuminated cannula assembly 102.

The optical fiber 110 may have any of a variety of configurations. In some embodiments, the optical fiber 110 may be described as a glass optical fiber. However, embodiments are not so limited. Rather, the optical fiber 110 may include other materials operable to transmit light, including, but not limited to, plastics, as may be desired for a particular application. In some embodiments, the optical fiber 110 may be a strand of optical fibers. In some embodiments, the optical fiber 110 extending between the light source 104 and the light sleeve 108 may include two more optical fibers coupled end to end, for example. While not shown, the optical fiber 110 may also include an outer cladding or other layers encircling the one or more optical fibers. For example, at least a portion of optical fiber 110 may be disposed in an outer cladding.

The optical fiber 110 is operable to conduct the light 112 therethrough. The light 112 conducted by the optical fiber 110 is conducted to the light sleeve 108 and emitted from the distal end 114 of the light sleeve 108. The optical fiber 110 is coupled to the light source 104 that is remote from the illuminated cannula assembly 102. In some embodiments, the light source 104 may be provided in a surgical console (not shown) to which the optical fiber 110 may be coupled. The light source 104 may include any light source operable to generate light for delivery through the optical fiber 110, including, but not limited to, a light-emitting diode (LED) light source, a phosphor light source, or a laser light source. Non-limiting examples of laser light sources may include monochromatic (e.g., infrared, visible), multi-spectral, or supercontinuum white lasers.

FIG. 2 illustrates an example illuminated cannula assembly 102. As illustrated, the illuminated cannula assembly 102 includes a cannula 106 and a light guide 200. In the illustrated embodiment, the cannula 106 includes a proximal hub 202 and tubing 204. The light guide 200 includes a light sleeve 108 and an optical fiber 110. The light sleeve 108 includes a proximal end 220, a distal end 114, and an exterior surface 222 extending between the proximal end 220 and the distal end 114. The light sleeve 108 also includes an end face 221 at the distal end 114. Light 112 may be emitted from the end face 221. In the illustrated embodiment, the light guide 200 also includes a transition region 206 disposed between the light sleeve 108 and the optical fiber 110, where the optical fiber 110 transitions from an elongated fiber to the tubular structure of the light sleeve 108. As illustrated, the transition region 206 branches from the light sleeve 108 at a location distal of the proximal hub 202 such that the transition region 206 is positioned adjacent to and distal of the proximal hub 202.

The proximal hub 202 includes an opening 208 and a through bore 212 in fluid communication with the opening 208. The opening 208 and through bore 212 are adapted to receive surgical instruments (e.g., an infusion line such as the infusion line 122 on FIG. 1). The opening 208 is disposed at a proximal end 210 of the proximal hub 202. The through bore 212 that extends from the opening 208 at the proximal end 210 to a distal end 214 of the proximal hub 202. As illustrated, the through bore 212 tapers along at least a portion of a length of the proximal hub 202 from the proximal end 210 to the distal end 214. However, the through bore 212 may have other configurations. For example, in some instances, the through bore 212 may have a constant cross-sectional size that conforms to a size of the opening 208. While not shown, the proximal hub 202 may include a valve for control of infusion liquids. For example, the proximal hub 202 may include a self-closing valve that seals around an inserted instrument and reseals upon removal of the instrument.

The tubing 204 extends from distal end 214 of the proximal hub 202 and defines an inner lumen 216. The inner lumen 216 is in fluid communication with the through bore 212. In some instances, the inner lumen 216 and the through bore 212 may form a continuous passage having a constant cross-sectional size. In other instances, the continuous passage may have a non-uniform cross-sectional size. The cannula 106, including proximal hub 202 and tubing 204, may be formed from materials such as, but not limited to, stainless steel, thermoplastics (e.g., polyamides, polycarbonates), stainless steel alloys, and titanium alloys. While not shown, surgical instruments (e.g., infusion lines such as the infusion line 122 of FIG. 1), liquids, medications, or other items may be introduced into an eye (e.g., the eye 118 shown in FIG. 1) through the passage defined by the inner lumen 216 and through bore 212.

The optical fiber 110 is operable to conduct light 112 to the light sleeve 108. The transition region 206 is disposed between a distal end 218 of the optical fiber 110 and a proximal end 220 of the light sleeve 108. The transition region 206 is operable to conduct the light 112 from the optical fiber 110 to the light sleeve 108. In some embodiments, the transition region 206 and the light sleeve 108 may form a unitary component. In other embodiments, the transition region 206 and the light sleeve 108 may be separate components that are coupled to each other. By way of example, the transition region 206 and the light sleeve 108 may be formed as a unitary component by injection molding or other manufacturing process. The transition region 206 may be formed of or include materials such as glass or plastics for transmission of the light 112. While not shown, the transition region 206 may also include an outer cladding or other layers, for example, to protect the transition region 206. In some instances, a portion of the transition region 206 may be disposed in the outer cladding. In other instances, an entirety of the transition region 206 may be disposed in the outer cladding. As explained above, the optical fiber 110 may also include an outer cladding or other layers encircling the one or more optical fibers.

The light 112 transmitted by the optical fiber 110 and received by the light sleeve 108 from the transition region 206 is transmitted along the length of the light sleeve 108 and emitted from the end face 221 of the light sleeve 108. In some embodiments (not shown), the light 112 may be emitted at one or more locations or along an entirety of the exterior surface 222. As illustrated, the light sleeve 108 may be disposed over the tubing 204 of the cannula 106. The light sleeve 108 may be formed of or include materials such as glass or plastics for transmission of the light 112. While not shown, the light sleeve 108 may also include an outer cladding or other layers, for example, to protect the light sleeve 108. In some instances, a portion of the exterior surface 222 of the light sleeve 108 may be disposed in the outer cladding. In other instances, an entirety of the light sleeve 108 may be disposed in the outer cladding. Further, in some instances, a continuous outer cladding may be formed over all or a portion of the optical fiber 110, the transition region 206, and the light sleeve 108.

FIG. 3A illustrates an end view of the distal end 114 of the light sleeve 108 in accordance with embodiments of the present disclosure. As illustrated, the tubing 204 is disposed in the light sleeve 108. The light sleeve 108 has an outer diameter $OD_1$ at the distal end 114. In some embodiments, the outer diameter $OD_1$ of the light sleeve 108 may range from about 0.2 millimeters to about 1 millimeter. The light sleeve 108 also has a thickness t. The thickness t of the light sleeve 108 may range from about 0.01 millimeters to about 0.5 millimeters, such that the light sleeve 108 may have an inner diameter Di that ranges from about 0.3 millimeters to about 1 millimeter. The tubing 204 has an inner diameter $ID_2$. The inner diameter $ID_2$ of the tubing 204 may define the size of the inner lumen 216. The inner diameter $ID_2$ may range from about 0.2 millimeters to about 0.9 millimeters. However, the scope of the disclosure is not so limited to these values of the outer diameter $OD_1$ of the light sleeve 108, thickness t of the light sleeve 108, $ID_1$ of the light sleeve 108, and $ID_2$ of the tubing 204. Rather, the light sleeve 108 and the tubing 204 may have any dimensions as desired for a particular application.

FIG. 3B illustrates an end view of the distal end 114 of the light sleeve 108 in accordance with alternative embodiments of the present disclosure. In the illustrated embodiment, the light sleeve 108 is disposed in the tubing 204.

Figure 4:
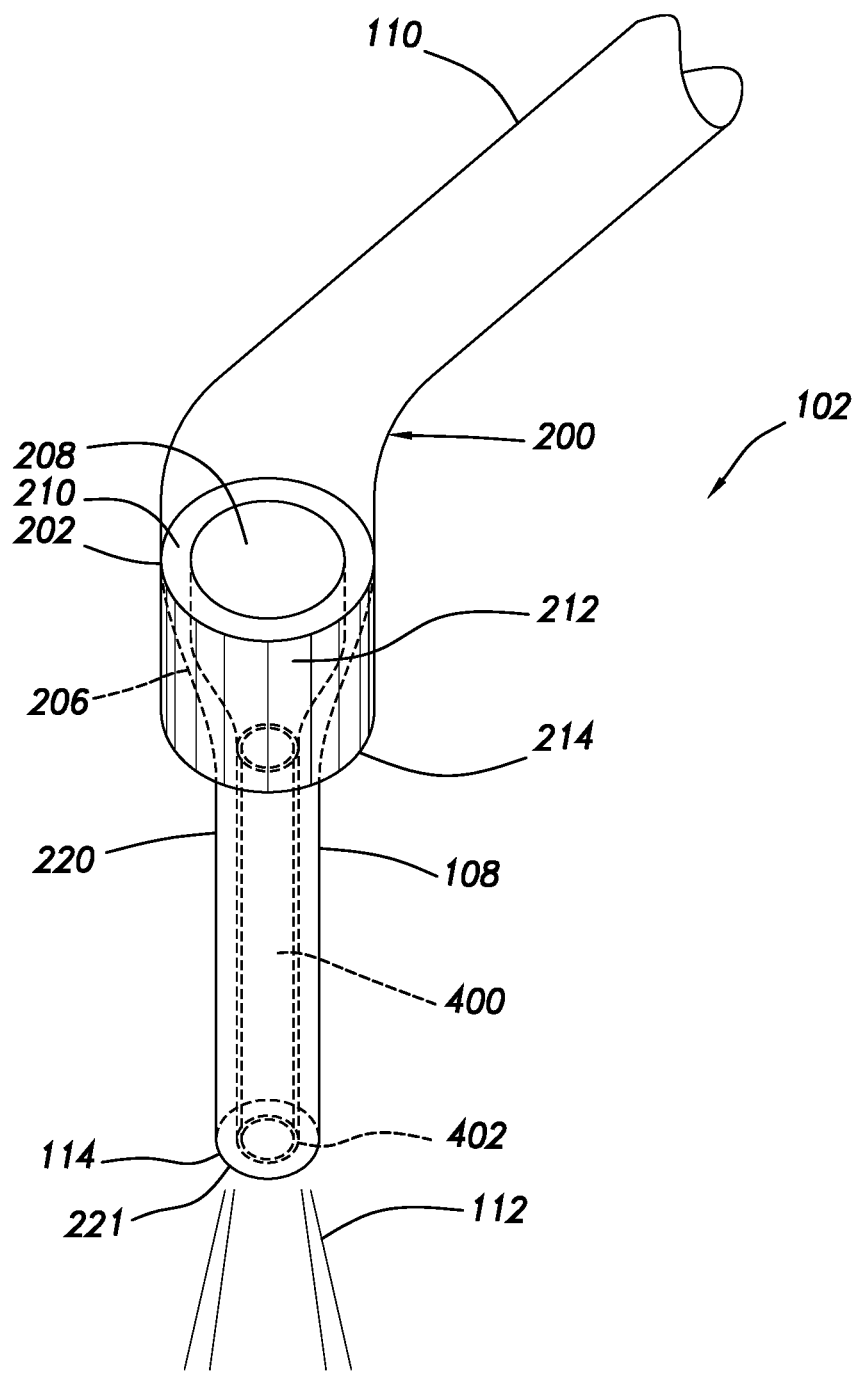
FIG. 4 illustrates another example illuminated cannula assembly.

FIG. 4 illustrates another example illuminated cannula assembly 102. In contrast to the embodiments shown on FIGS. 2 and 3, the example illuminated cannula assembly 102 shown in FIG. 4 omits the tubing 204 disposed in the light sleeve 108. In the present example shown in FIG. 4, though, the light sleeve 108 defines a lumen 400.

As illustrated, the illuminated cannula assembly 102 includes light guide 200 and proximal hub 202. In the illustrated embodiment, the light guide 200 includes the optical fiber 110, the transition region 206, and the light sleeve 108. The light 112 is transmitted along the optical fiber 110, through the transition region 206, and through the light sleeve 108 and is emitted from the distal end 114 of the light sleeve 108. Particularly, in some embodiments, the light 112 may be emitted from an end face 221 at the distal end 114 of the light sleeve 108. In some embodiments, the transition region 206 and the light sleeve 108 may be made as a unitary component. In other embodiments, the transition region 206 and the light sleeve 108 may be formed as separate components that are coupled together. The proximal hub 202 may be attached to the proximal end 220 of the light sleeve 108. In some embodiments, the transition region 206 and the optical fiber 110 may exclude an inner lumen. The proximal hub 202 and the light sleeve 108 may be coupled together in numerous ways including, for example, with the use of mechanical fasteners or adhesives. The proximal hub 202 includes an opening 208 and a through bore 212 in communication with the opening 208. The opening 208 and through bore 212 are configured to receive a surgical instrument (e.g., an infusion line such as the infusion line 122 shown in FIG. 1). The opening 208 is disposed at the proximal end 210 of the proximal hub 202, and the through bore 212 extends from the opening 208 at the proximal end 210 to a distal end 214 of the proximal hub 202. As illustrated, the through bore 212 tapers along at least a portion of a length of the proximal hub 202 from the proximal end 210 to the distal end 214. However, the through bore 212 may have other configurations. For example, in some instances, the through bore 212 may have a constant cross-sectional size that conforms to a size of the opening 208. The light sleeve 108 extends distally from the distal end 214 of the proximal hub 202 and terminates at the distal end 114. The light sleeve 108 defines the inner lumen 400 that fluidly communicates with the through bore 212 and the opening 208. In some instances, the inner lumen 400 and the through bore 212 may form a continuous passage having a constant cross-sectional size. In other instances, the continuous passage may have a non-uniform cross-sectional size. The light sleeve 108 may also include a distal opening 402 formed on the end face 221 so that fluids may be drawn into the inner lumen 400 or expelled from the inner lumen 400.

Figure 5:
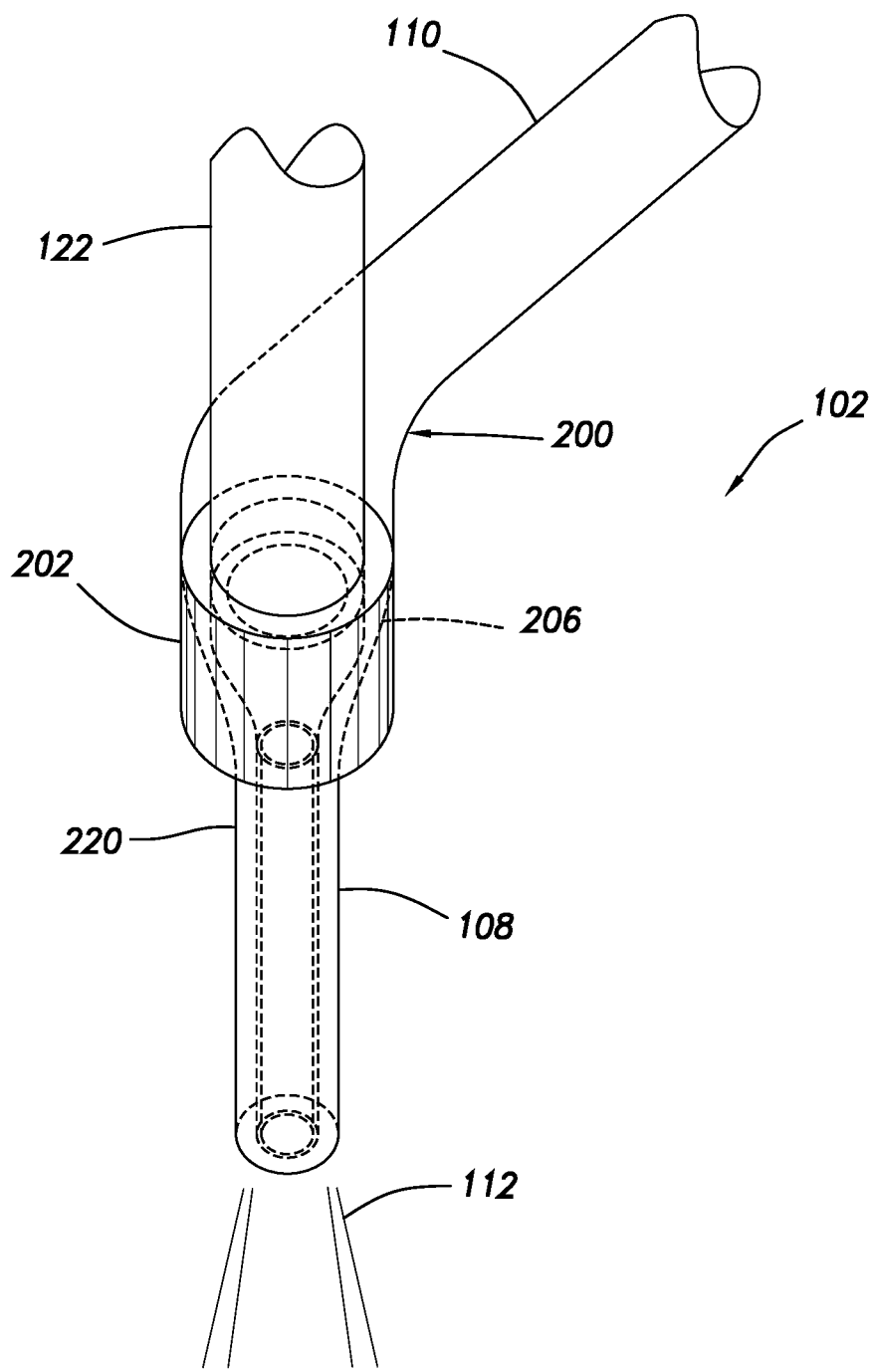
FIG. 5 illustrates another example illuminated cannula assembly with an infusion line.

FIG. 5 illustrates the illuminated cannula assembly 102 of FIG. 4 with an infusion line 122 inserted into the opening 208 and a portion of the through bore 212. Thus, the infusion line 122 is attached to the proximal hub 202. As illustrated, the illuminated cannula assembly 102 includes light guide 200 and proximal hub 202. The light guide 200 includes the optical fiber 110, the transition region 206, and the light sleeve 108. The proximal hub 202 is attached to the proximal end 220 of the light sleeve 108. The infusion line 122 may be used, for example, to introduce fluids through the light sleeve 108 and into an eye (e.g., such as eye 118 shown in FIG. 1). In this manner, the light sleeve 108 is operable to introduce fluids, as well as provide illumination into an eye. Any of a variety of different fluids may be introduced through the infusion line 122, including, but not limited to, irrigation fluids, such as a balanced salt solution.

As previously described with respect to the examples shown in FIGS. 2, 4, and 5, the light guide 200 may include a transition region 206. The transition region 206 may be designed, for example, to enable light to transfer from the optical fiber 110 and into the light sleeve 108, ultimately emanating from the light sleeve 108, for example, an end face 221 formed at the distal end 114. In the transition region 206, it is desirable to avoid loss of any of the light 112 from the transition region 206 so a maximum amount of the light 112 is emitted from the end face 221 at the distal end 114. In some instances, the light 112 may include white light. In other instances, the light 112 may include any other desired frequency or frequencies of light.

Figure 6:
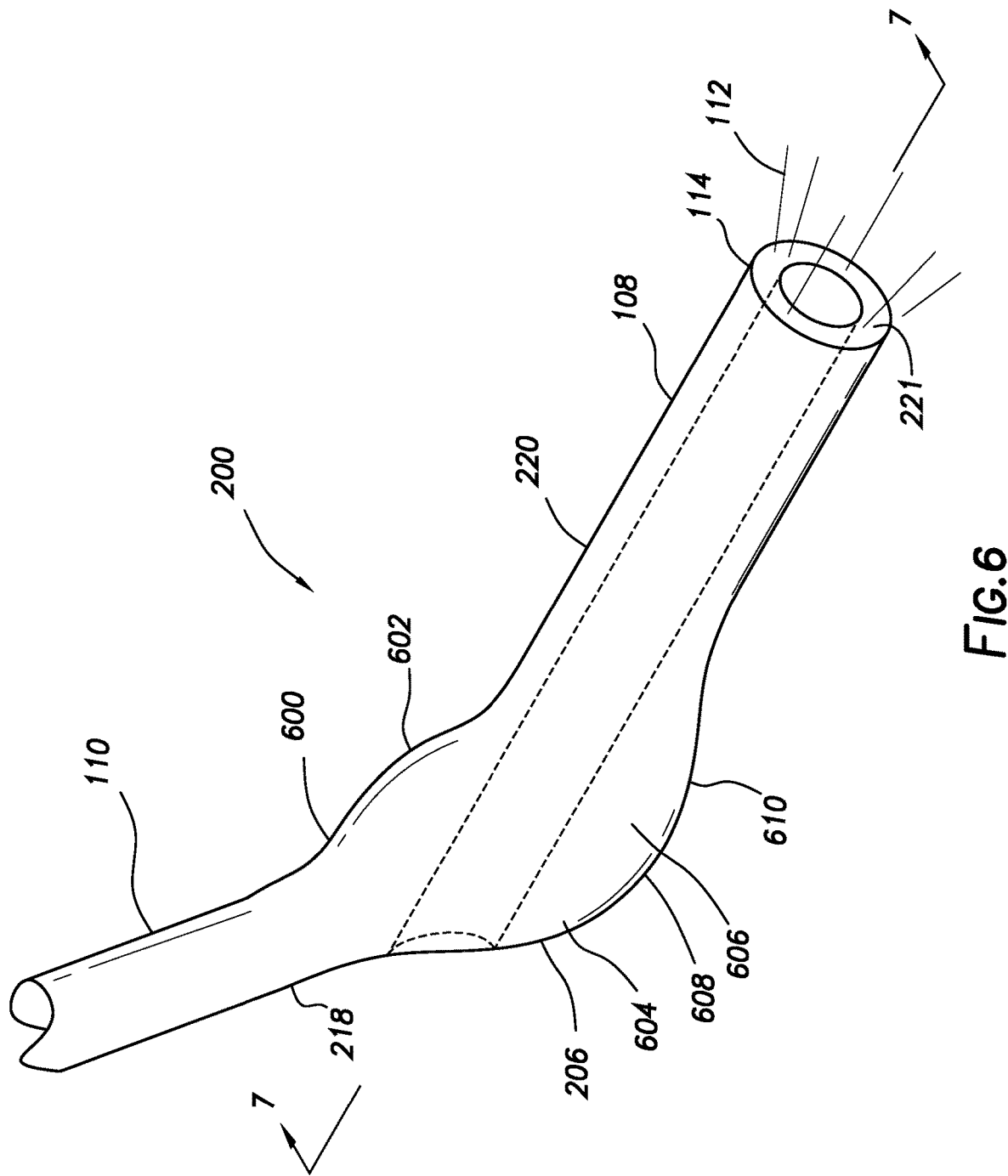
FIG. 6 illustrates an example light guide.

FIG. 6 shows an example embodiment of a transition region 206 of a light guide 200. For simplicity, the example light guide 200 is shown without a tubing (e.g., tubing 204 shown in FIG. 2) that may be disposed in the light sleeve 108. As illustrated, the light guide 200 includes an optical fiber 110, a transition region 206, and a light sleeve 108. The light sleeve 108 includes a proximal end 220, a distal end 114, and an end face 221 disposed at the distal end 114. The optical fiber 110 fiber includes a distal end 218. The transition region 206 couples the optical fiber 110 and the light sleeve 108. The light 112 transmitted through the optical fiber 110 passes through the transition region 206 and into the light sleeve 108. The light 112 is emitted from the end face 221 disposed at the distal end 114 of the light sleeve 108. The transition region 206 is coupled to the optical fiber 110 at the distal end 218. The transition region 206 may be secured to the optical fiber 110 in any applicable manner. In some embodiments, the transition region 206 and the optical fiber 110 may be formed as a unitary component. In other embodiments, the transition region 206 and the optical fiber 110 may be separately formed components that are joined together. The transition region 206 is coupled to the light sleeve 108 at the proximal end 220. The transition region 206 may be coupled to the light sleeve 108 in any applicable manner. In some embodiments, the transition region 206 and the light sleeve 108 may formed as a unitary component. Thus, in some embodiments, the light guide 200 may be formed as a unitary component. In other embodiments, the transition region 206 and the light sleeve 108 may be formed as separate components that are joined together.

As shown in the example of FIG. 2, tubing 204 may be disposed in the light sleeve 108. In some embodiments, the tubing 204 may extend beyond the transition region 206. For example, in some embodiments, the tubing 204 may extend distally beyond the transition region 206 As shown in FIG. 6, the transition region 206 includes an elongated body portion 600 coupled to the optical fiber 110. The elongated body portion 600 splits such that the transition region 206 includes a first branch 602 and a second branch 604 that split at a location proximal to the tubing 204, wrap around the tubing 204, and join at a location along a length of the tubing 204. The first branch 602 and the second branch 604 may join at an enlarged portion 606 in the transition region 206. As illustrated, the enlarged portion 606 includes a bulge 608. The bulge 608 assists in guiding the light 112 from the optical fiber 110 without an inner lumen to the light sleeve 108 that includes an inner lumen 400 without undesired loss of the light 112 that would degrade performance and/or efficiency, e.g., by reducing an amount of light 112 emitted from the end face 221 at the distal end 114 of the light sleeve 108.

FIG. 7 is a cross-sectional view of the light guide 200 shown in FIG. 6 taken along line 7-7. As illustrated, the light guide 200 includes the optical fiber 110, the transition region 206, and the light sleeve 108. As previously described, the transition region 206 is disposed between the optical fiber 110 and the light sleeve 108 and is operable to transmit the light 112 from the optical fiber 110 to the light sleeve 108. The distal end 218 of the optical fiber is coupled to the transition region 206. The proximal end 220 of the light sleeve 108 is coupled to the transition region 206. The transition region 206 of the light guide 200 includes the elongated body portion 600, the first branch 602 (shown, for example, in FIGS. 6 and 8), the second branch 604 (shown, for example, in FIGS. 6 and 8), and the enlarged portion 606. The first and second branches 602 and 604 are shown in more detail in the cross-sectional view of FIG. 8. The transition region 206 also includes a transition inner lumen 700. As illustrated, the transition inner lumen 700 extends along a longitudinal axis 702 of the light sleeve 108 and joins and is in fluid communication with the inner lumen 400 of the light sleeve 108. The inner lumen 400 also extends along the longitudinal axis 702. The inner lumen 400 of the light sleeve 108 and the transition inner lumen 700 join at the proximal end 220 of the light sleeve 108. The distal opening 402 of the light sleeve 108 provides for the passage of fluids out of the light sleeve 108.

The enlarged portion 606 may include a bulge 608. As best seen on FIG. 7, the bulge 608 is enlarged relative to a cross-sectional size of the light sleeve 108. FIG. 8 is a cross-sectional view of the light guide 200 through the enlarged portion 606 taken along line 8-8 at the enlarged portion 606 and, particularly, at the bulge 608. As shown in FIG. 8, the enlarged portion 606 of the transition region 206 has a thickness $t_1$ that is greater than a thickness $t_2$ of the transition region 206 opposite the bulge 608. FIG. 8 shows the first branch 602 and the second branch 604 formed on opposing sides of the transition inner lumen 700. The first and second branches 602 and 604 combine to form the enlarged portion 606. At the cross-section shown in FIG. 8, the transition region 206 has an outer diameter $OD_2$, a first thickness $t_1$, and a second thickness $t_2$, as shown. It should be understood that the outer diameter $OD_2$ of the transition region 206 varies along a length thereof. In some embodiments, the outer diameter $OD_2$ may be larger than $OD_1$ of the light sleeve 108, as shown in FIGS. 3A and 9. For example, $OD_2$ may be at least about 5% larger than $OD_1$, at least about 10% larger than $OD_1$, at least about 20% larger than $OD_1$, at least about 30% larger than $OD_1$, or at least about 50% larger than $OD_1$. The first thickness $t_1$ of the transition region 206 at the bulge 608 may range from 0.05 millimeters to about 0.5 millimeters. The second thickness $t_2$ of the transition region 206 opposite the bulge 608 may be less than the thickness $t_1$. In some embodiments, the thickness $t_2$ may range from about 0.1 millimeters to about 0.5 millimeters. However, the scope of the disclosure is not limited to these example values of the outer diameter $OD_2$ of the transition region 206, thickness $t_1$ of the transition region 206, and thickness $t_2$ of the transition region 206. Rather, the transition region 206 may have other dimensions as desired for a particular application.

FIG. 9 is a cross-sectional view of the light sleeve 108 at the distal end 114 thereof taken along line 9-9. The light sleeve 108 has an outer diameter $OD_1$ at the distal end 114. As explained above, the outer diameter $OD_1$ of the light sleeve 108 at the distal end 114 is less than the outer diameter $OD_2$ of the transition region 206 shown on FIG. 8. In some embodiments, the outer diameter $OD_1$ may be about 5%, about 10%, about 20%, about 30%, or about 50% of the outer diameter $OD_2$. In other instances, the $OD_1$ may be smaller than the $OD_2$ by greater than 50%. In some embodiments, the outer diameter $OD_1$ of the light sleeve 108 at the distal end 114 may range from about 0.01 millimeters to about 0.5 millimeters, while the outer diameter $OD_2$ of the transition region 206 may larger than $OD_1$. For example, $OD_2$ may be at least about 5% larger than $OD_1$, at least about 10% larger than $OD_1$, at least about 20% larger than $OD_1$, at least about 30% larger than $OD_1$, or at least about 50% larger than $OD_1$.

The illuminated cannula assemblies described herein may be used for illumination during an eye surgery. By providing illumination with the illuminated cannula assemblies, additional devices and/or fluids may also be introduced through the illuminated cannula assemblies, thus eliminating the need for an additional incision for the introduction of a dedicated illumination device.

Although the disclosure provides numerous examples, the scope of the present disclosure is not so limited. Rather, a wide range of modification, change, and substitution is contemplated in the foregoing disclosure. It is understood that such variations may be made to the foregoing without departing from the scope of the present disclosure.

What is claimed is:

1. An illuminated cannula assembly comprising:
   a light guide comprising:
      an optical fiber;
      a light sleeve; and
      a transition region,
   the transition region joining the optical fiber and the light sleeve for transmitting light from the optical fiber to the light sleeve, wherein the light sleeve is configured to emit the light from a distal end thereof; and
   a cannula comprising:
      a tubing, wherein the light sleeve is disposed around the tubing,
   wherein the transition region branches to form a first branch and a second branch that wrap around the tubing and join to form an enlarged portion of the transition region along a first side of the tubing opposite the optical fiber and a reduced portion on a second side opposite the first side, wherein the enlarged portion comprises a bulge.

2. The illuminated cannula assembly of claim 1, wherein the cannula further comprises a proximal hub disposed at a proximal end of the tubing.

3. The illuminated cannula assembly of claim 1, wherein the transition region further comprises:
   an elongated body portion coupled to a distal end of the optical fiber;
   wherein the first branch and the second branch split from the elongated body portion to form a transition inner lumen that extends along the transition region, wherein the first branch and the second branch join to form the enlarged portion of the transition region along a first side of the transition inner lumen and the reduced portion on a second side of the transition inner lumen opposite the first side of the transition inner lumen.

4. The illuminated cannula assembly of claim 3, wherein an outer diameter of the transition region at the bulge is at least 20% larger than an outer diameter of the light sleeve at the distal end of the light sleeve.

5. The illuminated cannula assembly of claim 3, wherein the light sleeve defines an inner lumen, and wherein the inner lumen is in fluid communication with the transition inner lumen.

6. A surgical illumination system comprising:
   a light source operable to generate light;
   an illuminated cannula assembly operable to receive the light generated by the light source, the illuminated cannula assembly comprising:
      a light guide comprising:
         an optical fiber coupled to the light source;
         a light sleeve; and
         a transition region joining the optical fiber and the light sleeve, the transition region being configured to transmit the light from the optical fiber to the light sleeve and the light sleeve being operable to emit the light from a distal end thereof; and
      a cannula comprising:
         a tubing, and
         a proximal hub disposed at a proximal end of the tubing, the light sleeve being disposed around the tubing,
   wherein the transition region branches to form a first branch and a second branch that encircle around the tubing and join to form an enlarged portion of the transition region along a first side of the tubing opposite a second side that is coupled to the optical fiber and a reduced portion on the second side, wherein the enlarged portion comprises a bulge.

7. The system of claim 6, wherein the proximal hub comprises:
   an opening formed at a proximal end of the proximal hub; and
   a through bore that extends from the opening to a distal end of the proximal hub.

8. The system of claim 7, wherein the through bore is tapered.

9. The system of claim 6, wherein the transition region of the light guide is adjacent to the proximal hub.

10. The system of claim 6, wherein an outer diameter of the transition region at the bulge is at least 20% larger than an outer diameter of the light sleeve at the distal end of the light sleeve.

* * * * *